US011547559B2

(12) United States Patent
Liu et al.

(10) Patent No.: US 11,547,559 B2
(45) Date of Patent: Jan. 10, 2023

(54) VALVE PROSTHESIS

(71) Applicant: SHANGHAI MICROPORT CARDIOFLOW MEDTECH CO., LTD., Shanghai (CN)

(72) Inventors: Shihong Liu, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 0 days.

(21) Appl. No.: 16/474,490

(22) PCT Filed: Sep. 28, 2017

(86) PCT No.: PCT/CN2017/103902
§ 371 (c)(1),
(2) Date: Jun. 27, 2019

(87) PCT Pub. No.: WO2018/120949
PCT Pub. Date: Jul. 5, 2018

(65) Prior Publication Data
US 2019/0336279 A1    Nov. 7, 2019

(30) Foreign Application Priority Data
Dec. 28, 2016  (CN) .......................... 201611238574.8

(51) Int. Cl.
*A61F 2/24* (2006.01)
(52) U.S. Cl.
CPC .......... *A61F 2/2418* (2013.01); *A61F 2/2409* (2013.01); *A61F 2/2463* (2013.01); *A61F 2230/0069* (2013.01)

(58) Field of Classification Search
CPC ............................ A61F 2/2418; A61F 2/2409
See application file for complete search history.

(56) References Cited

U.S. PATENT DOCUMENTS

2006/0259136 A1   11/2006  Nguyen et al.
2014/0005777 A1*   1/2014  Anderl .................. A61F 2/2445
                                                                    623/2.18
(Continued)

FOREIGN PATENT DOCUMENTS

CN         1961845 A     5/2007
CN       102113921 A     7/2011
(Continued)

Primary Examiner — Leslie Lopez
(74) Attorney, Agent, or Firm — Muncy, Geissler, Olds & Lowe, P.C.

(57) ABSTRACT

A valve prosthesis (10), comprising a stent (1), a leaflet (2), and a skirt (3); the stent (1) comprises an inflow end, an outflow end, and a plurality of wavy segments axially connected; the wavy segments comprise a plurality of reticular structure units disposed circumferentially; the leaflet (2) and the skirt (3) are fixed on the stent (1) respectively; the upper portion of the skirt (3) is provided with indentations (321); the skirt (3) is fixed with the leaflet (2) by means of the indentations (321); the skirt (3) further comprises first protrusion portions (323) extending toward the direction of the outflow end of the stent; one ends of the first protrusion portions (323) are connected with the indentations (321), and the other ends of the first protrusion portions are fixed to the stent (1); by such a way, the connection strength of the skirt (3) and the stent (1) is enhanced; and besides, when the valve prosthesis (10) is implanted at a lower position, perivalvular leakage preventing height can be increased by means of the first protrusion portions (323), thereby avoiding the leakage of a part of blood from the stent (1) and further improving the perivalvular leakage preventing effect.

15 Claims, 9 Drawing Sheets

(56) References Cited

U.S. PATENT DOCUMENTS

| | | | |
|---|---|---|---|
| 2014/0228945 A1 | 8/2014 | Valdez et al. | |
| 2014/0277417 A1* | 9/2014 | Schraut | A61F 2/2403 623/2.17 |
| 2015/0081013 A1* | 3/2015 | Braido | A61F 2/89 623/2.18 |
| 2015/0127100 A1 | 5/2015 | Braido et al. | |
| 2015/0157455 A1 | 6/2015 | Hoang et al. | |
| 2015/0209141 A1 | 7/2015 | Braido et al. | |

FOREIGN PATENT DOCUMENTS

| | | |
|---|---|---|
| CN | 102949253 A | 3/2013 |
| CN | 103006352 A | 4/2013 |
| CN | 103237524 A | 8/2013 |
| JP | 2008539985 A | 11/2008 |
| JP | 2013543406 A | 12/2013 |
| JP | 2016538949 A | 12/2016 |

\* cited by examiner

VALVE PROSTHESIS

TECHNICAL FIELD

The present application relates to the field of medical instruments and, in particular, to a valve prosthesis.

BACKGROUND

With the prolongation of human lives and the aging of population, the incidence of valvular diseases has been continuously increasing. According to foreign report, in European and American countries, 2%-7% of people aged over 65 have valvular disease which ranks the third and is next to the coronary heart disease and hypertension. Thousands of patients benefit from surgical valve replacement every year. However, even in developed countries, there are still a large number of patients with severe valvular disease that cannot receive the surgical treatment due to many reasons including late disease stages, advanced ages and various complications. The advent of transcatheter valve prostheses, as well as the increasing improvement of their performance, has undoubtedly brought good news to these patients, providing an effective therapeutic method.

Studies have shown that this new technique is safe and effective for patients being unable to receive the surgical valve replacement or having a high risk in surgical valve replacement. By contrast to the surgical operation, transcatheter valve replacement does not require sternotomy and extracorporeal circulation support, and is an easily accepted treatment having minimal invasion, less complications, quick postoperative recovery and less patient pain.

After continuous evolution, there have been several transcatheter valve prostheses applied to clinical practice. However, these existing products still have some drawbacks and imperfections.

SUMMARY

It is an object of the present application to provide a valve prosthesis to mitigate paravalvular leakage (PVL) and thrombosis after implanting a valve.

To this end, the present application provides a valve prosthesis comprising a stent, leaflets and a skirt, wherein the stent comprises an inflow end, an outflow end and a plurality of axially connected wavy segments, each of the wavy segments comprising a plurality of reticular structure cells arranged circumferentially, each of the leaflet and the skirt being fixed to the stent, An upper portion of the skirts provided with a notch, and the skirt is fixed to the leaflet by means of the notch, wherein the skirt further comprises first protrusion(s) extending toward the outflow end of the stent, one end of the first protrusion being connected to the notches, the other end of the first protrusion being fixed to the stent.

Preferably, the other end of the first protrusion is located at ½ to ⅔ of a height of the leaflet.

Preferably, a number of the first protrusions is no more than a number of reticular structure cells of a corresponding wavy segments of the stent to which the first protrusions are fixed.

Preferably, the number of the first protrusions ranges from 1 to 9.

Preferably, the upper portion of the skirt is provided with a plurality of the notches, each of the notches being fixed to one leaflet, and the number of the first protrusion(s) in one notch is no more than three.

Preferably, the first protrusion has a serrated, trapezoidal or sinusoidal shape Preferably, the skirt may further comprise second protrusion(s), one end of the second protrusion being connected to a lower portion of the skirt, the other end of the second protrusion being fixed to the inflow end of the stent.

Preferably, the second protrusion has a serrated, trapezoidal or sinusoidal shape.

Preferably, a number of the second protrusions is no more than a number of reticular structure cells circumferentially arranged at the inflow end of the stent.

Preferably, the number of the second protrusions ranges from 3 to 12.

Preferably, the skirt is comprised of at least one skirt segment, each of the at least one skirt segment having an upper edge and a lower edge, wherein the notch is disposed on the upper edge of the skirt segment and a border of the notch comprises a leaflet fixing edge.

Preferably, the leaflet fixing edge comprises an inwardly concaved and curved structure protruding toward the lower edge.

Preferably, the skirt further comprises a foldable flap arranged outside the stent.

Preferably, the skirt may be comprised of at least one skirt segment, each of the at least one skirt segment having an upper edge and a lower edge, wherein the notch is disposed on the upper edge of the skirt segment, and a border of the notch comprises a leaflet fixing edge, wherein the skirt segment comprises a body and a foldable flap portion extending from the body toward the inflow end of the stent, wherein the foldable flap portion forms the foldable flap structure, and the lower edge of the skirt segment defines an edge of the foldable flap portion.

Preferably, the skirt further comprises a second protrusion, one end of the second protrusion being connected to the edge of the foldable flap portion, the other end of the second protrusion being fixed to the stent at an outer side of the stent.

Preferably, the other end of the second protrusion is fixed to a corresponding reticular structure cell of a first row of the wavy segment from the inflow end of the stent.

Preferably, a length of the body of the skirt segment is 1.5 to 2 times as long as a length of the foldable flap portion.

Preferably, lateral sides of the skirt segment are joined togetherto form joint line(s), wherein a joint line of the foldable flap portion comprises a straight line extending toward the outside of the stent or a curved line protruding toward the outside of the stent.

Preferably, each of the notches comprises two notch sections, and the two sections are located at adjacent upper edges of adjacent skirt segments or located at left and right upper edges of one skirt segment.

Preferably, a border of the notch sections comprises a sub-leaflet fixing edge, and the sub-leaflet fixing edge comprises an inwardly concaved and curved structure protruding toward the lower edge of a corresponding skirt segment.

Preferably, a radius of curvature of adjoining the sub-leaflet fixing edges is equal at joint ends thereof.

Preferably, lengths of adjoining sub-leaflet fixing edges are in a ratio ranging from 1:3 to 3:1.

Preferably, the first protrusion is located in a corresponding notch section and the first protrusion has a serrated, trapezoidal, sinusoidal, right-angled triangular or right-angled trapezoidal shape.

In summary, in the valve prosthesis of the present application, the upper portion of the skirt is provided with a first protrusion extending toward the outflow end of the stent and being fixed to the stent. In such a way, on one hand, the connection between the skirt and the stent is able to be strengthened. On the other hand, when the valve prosthesis is implanted slightly lower position than desired, the first protrusion is able to increase preventing height of paravalvular leakage, thereby avoiding the leakage of a part of blood from the stent, and further improving the paravalvular leakage preventing effect.

In particular, the other end of the first protrusion is located at ½ to ⅔ of the height of the leaflets. This enables an increased paravalvular leakage preventing height, ensures a normal operation of valve prosthesis, cuts down skirt's material and reduces the risk of thrombosis formation.

In these figures,
10—valve prosthesis; 1—stent; 2—leaflet; 3—skirt; 31, 31'—skirt segment; 311—body; 312—foldable flap portion; 32, 32'—upper edge of skirt; 321—notch; 321a—first notch section; 321b—second notch section; 322, 322'—leaflet fixing edge; 322a—first sub—leaflet fixing edge; 322b—second sub—leaflet fixing edge; 33, 33'—lower edge of skirt; 34—joint line; 35—extension edge; 323, 323a, 323b—first protrusion; 331—second protrusion; I—border line; 20—valve ring.

DETAILED DESCRIPTION

The valve prosthesis proposed by the present application will be further described in detail below with reference to the accompanying drawings 1-8, to make the purpose, advantages and features of the present application more apparent. It should be noted that the drawings are in a very simplified form and not necessarily presented to scale, for the only purpose to facilitate convenient and explicit description of embodiments of the present application.

As used herein, the terms "proximal", "bottom", "lower", "distal", "top" and "upper" are used with respect to a direction in which blood in the heart flows through the valve prosthesis. While not intended to be limited, a "proximal", "bottom" or "lower" end refers to an end close to the blood flowing into the valve prosthesis, and a "distal", "top" or "upper" end refers to an end close to the blood flowing out of the valve prosthesis.

Unless explicitly specified, the singular forms of "a," "an", and "the" used herein and in the appended claims, include plural objects. Unless explicitly specified, the term "or" used herein and in the appended claims generally refers to "and/or". In addition, an "inner", "interior" or "internal" side refers to a side of the stent away from the human tissues, and an "outer", "exterior" or "external" side refers to a side of the stent close to the human tissues.

Further, the valve prosthesis of present application may be implemented particularly as an interventional prosthetic heart valve for replacing a diseased valve, but the present application is not limited thereto. The valve prosthesis of present application will be described in greater details below with reference to specific embodiments.

Embodiment 1

Figure 1:
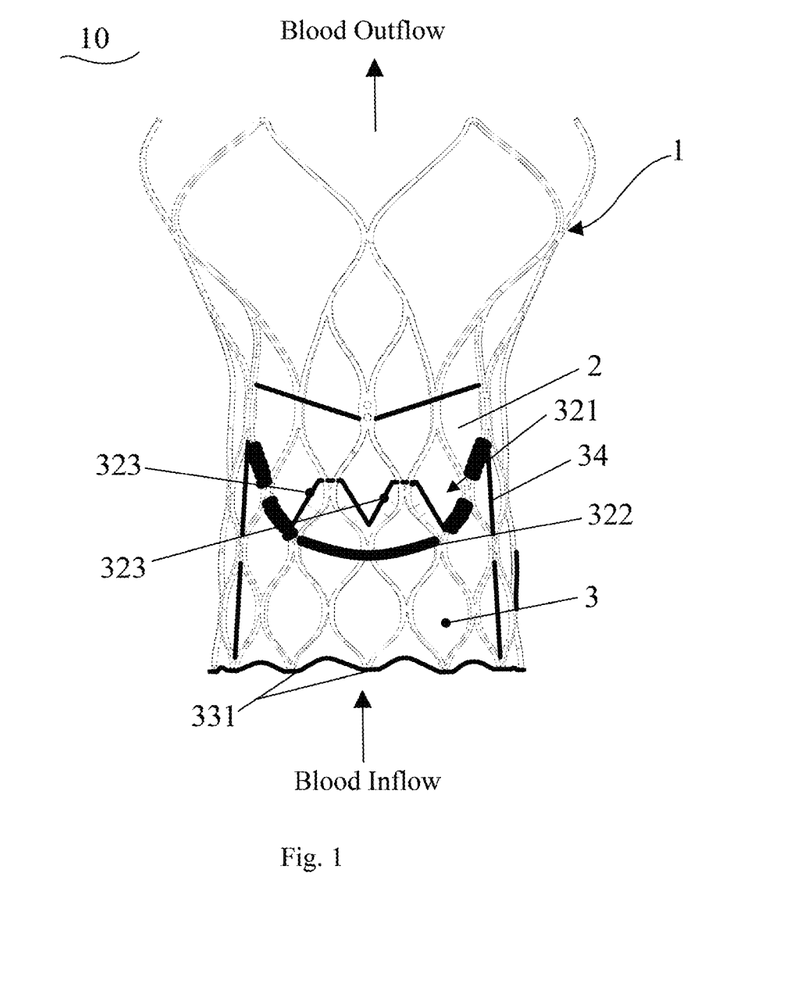
FIG. 1 is a schematic illustration of a valve prosthesis in an expanded state according to embodiment 1 of the present application.
Figure 2:
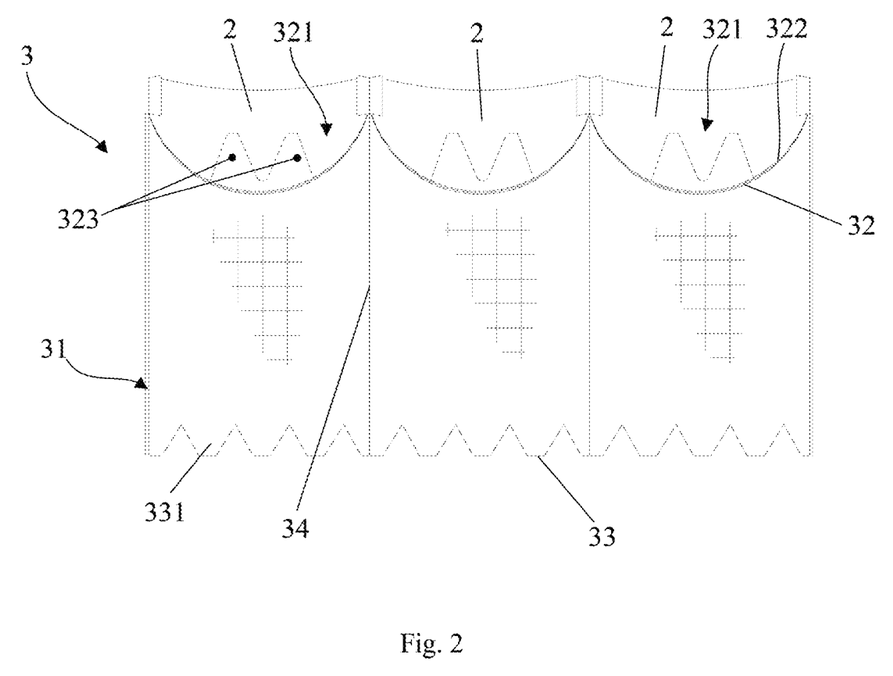
FIG. 2 is a schematic illustration of a skirt assembled with a leaflet according to embodiment 1 of the present application.
Figure 3:
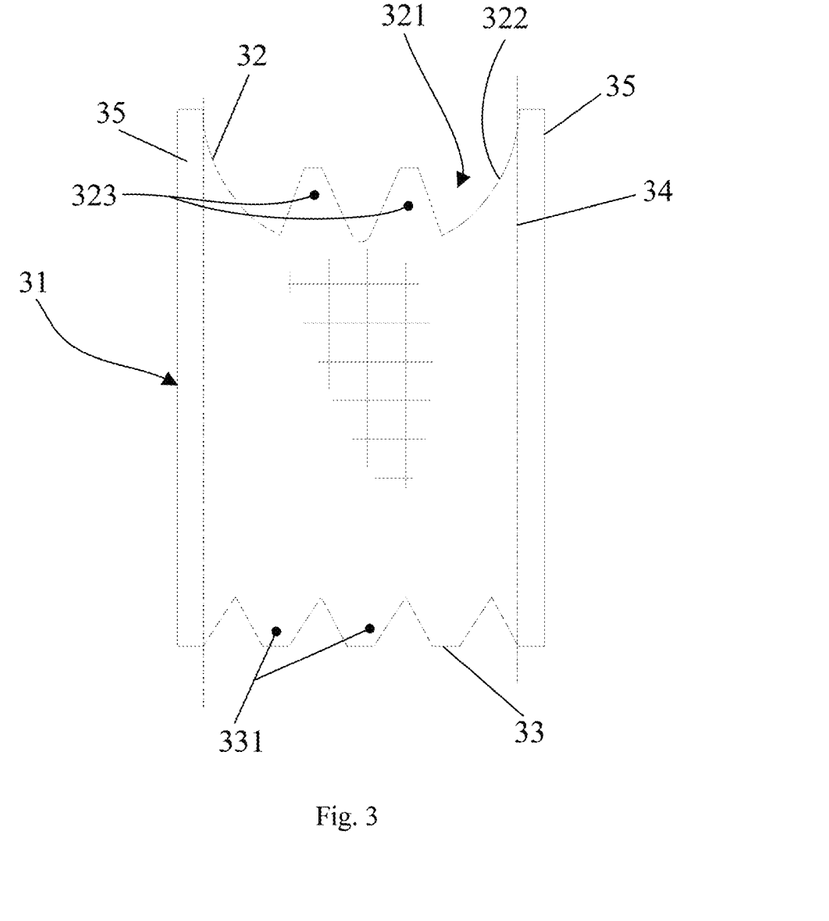
FIG. 3 is a schematic illustration of a skirt segment according to embodiment 1 of the present application.

Reference is now made to FIGS. 1-3, in which FIG. 1 is a schematic illustration of a valve prosthesis in an expanded state according to embodiment 1 of the present application, FIG. 2 is a schematic illustration of a skirt assembled with a leaflet according to embodiment 1 of the present application, and FIG. 3 is a schematic illustration of a skirt segment according to embodiment 1 of the present application.

As shown in FIGS. 1-3, the valve prosthesis 10 includes a stent 1, leaflets 2 and a skirt 3. According to the present application, the stent 1 includes an inflow end and an outflow end with the direction from the inflow end to the outflow end defined as an axial direction of the stent. There are at least three pieces of leaflet 2 sequentially connected and fixed to the stent 1. A notch 321 is provided in the upper portion of the skirt 3. The skirt 3 is fixed to the leaflet 2 by means of the notch 321. The skirt 3 further includes first protrusion(s) 323 extending toward the outflow end of the stent 1, one end of the first protrusion 323 being connected to the notch 321, the other end of the first protrusion 323 being secured to the stent 1. The outflow end corresponds to the direction in which blood flows out, and the inflow end corresponds to the direction in which blood flows in.

In the present application, the stent 1 further includes a plurality of axially connected wavy segments, each of the wavy segments comprising a plurality of reticular structure cells arranged circumferentially, each of the reticular structure cells being constructed from a plurality of wavy rods connected end-to-end. Those skilled in the art can suitably choose the number of wavy segments, as well as the shape, size, density of the reticular structure cells of each wavy segment, and width and size of the wavy rods, depending on requirements. In the present application, the first protrusion 323 is fixed to the stent 1, which is able to strengthen connection between the skirt 3 and the stent 1, as well as increase a height to prevent paravalvular leakage to improve paravalvular leakage preventing effect with an ensured connection strength, when the valve prosthesis 10 is implanted at a lower position than desired. Apparently, the first protrusion 323 and the skirt 3 may be manufactured separately.

Further, as shown in FIG. 2, the skirt 3 is comprised of at least one skirt segment 31. In this case, the notch 321 is arranged at an upper edge 32 of the skirt segment 31. Generally, the fixed connection between the leaflet 2 and the skirt 3 may be achieved by virtue of the notch 321. The number of the notches 321 is not necessarily related to the number of the skirt segments 31 constituting a skirt 3. A plurality of notches 321 may be disposed on one skirt segment 31, or none of the notches 321 is arranged on one skirt segment 31. Additionally, the border of the notch 321 comprises a leaflet fixing edge 322 to match with a corresponding leaflet 2 (see FIG. 1). The leaflet fixing edge 322 has a shape of an inward concave curve protruding toward a lower edge 33 of the corresponding skirt segment 31, the curve preferably being an arc, such as an arc with a symmetric center. Preferably, the shape of the leaflet fixing edge 322 matches the shape of the leaflets 2.

In this embodiment, the skirt 3 is comprised of three sequentially connected skirt segments 31. In this embodiment, the number of the leaflets 2 is three. Each of the three skirt segments 31 has an upper edge 32 and an opposing lower edge 33, and the notch 321 is located at the upper edge 32 of the skirt segment 31. In addition, the border of the notch 321 comprises a leaflet fixing edge 322 to match with a corresponding leaflet 2 (see FIG. 2).

In an exemplary process, the leaflets 2 are first sutured to the skirt 3, and both are then mounted to the expandable stent 1, thereby forming the valve prosthesis 10. The skirt 3 is sutured to the stent 1 along the upper edge 32 and lower edge 33 of the individual skirt segment 31, thereby achieving the fixation between the skirt 3 and the stent 1.

In addition, one skirt segment 31 may be joined with others at its opposing lateral sides, defining a joint line 34 that limits the sutures (the joint line 34 is not an actual suture line in suture operation). In this embodiment, each of the opposing lateral sides of the skirt segment 31 further includes a flap 35 (see FIG. 3), which facilitates the connection to the adjacent skirt segment 31 and forms the joint line 34. The joint line 34 may be either linear or non-linear, depending on the lateral outline of the stent 1. Such an arrangement allows the skirt 3 to closely fit on the stent 1 during assembly.

In a preferred example, the other end of the first protrusion 323 is located at ½ to ⅔ of the height of the corresponding leaflet 2 (as can be more clearly seen in FIG. 1). This arrangement enables an increased paravalvular leakage preventing height, ensures a normal operation of valve prosthesis, cuts down skirt's material and reduces the risk of thrombosis formation. It is noted that the height of the leaflet 2 refers to the maximum linear distance from lower edge (i.e., the location of the connection with the notch 321) of the leaflet 2 fixed to the stent 1 to the upper edge (i.e., the end close to the outflow end of the stent 1) of the leaflet 2 along the axial direction of the stent 1. Accordingly, the other end of the first protrusion 323 refers to one end closing to the outflow end of the stent 1 after the first protrusion 323 is secured to the stent 1.

Further, the present application is not limited to any particular shape of the first protrusion 323, as long as the first protrusion 323 covers at least part of the reticular structure cells of the stent 1. Preferably, the first protrusion 323 has a saw-tooth, trapezoidal, sinusoidal or other analogous shape. In suture, the first protrusion 323 is sutured to at least two wavy rods constituting a corresponding reticular structure cell to secure the first protrusion 323 to the stent 1.

Further, the number of the first protrusions 323 depends on the number of reticular structure cells of the wavy segment to which the stent 1 is fixed. In one example, the number of the first protrusions 323 is equal to or less than the number of reticular structure cells of the said wavy segment. Preferably, the number of the first protrusion(s) 323 of the skirt 3 ranges from 1 to 9, and more preferably, the first protrusions 323 are circumferentially and uniformly distributed. Preferably, the number of first protrusions 323 in one notch 321 is no more than three, preferably two to three.

In another example, the skirt 3 further includes second protrusion(s) 331, one end of the second protrusion 331 being connected to the lower portion of the skirt 3, the other end of the second protrusion 331 being fixed to the inflow end of the stent 1. Specifically, as shown in FIG. 1 and FIG. 3, the second protrusion 331 is arranged on the lower edge 33 of the skirt segment 31, which extends toward and is fixed to the inflow end of the stent 1. There is no particular limitation to the shape of the second protrusion 331, which preferably has a saw-tooth, trapezoidal, sinusoidal or other analogous shape. Preferably, the number of the second protrusions 331 depends on the number of reticular structure cells circumferentially arranged at the inflow end of the stent 1. In one example, the number of the second protrusions 331 is equal to or less than the number of the said reticular structure cells and preferably ranges from 3 to 12.

In this embodiment, the fixation between the leaflet 2 and the skirt 3, between the skirt 3 and the stent 1, between the leaflet 2 and the stent 1, between the individual leaflet 2 and between individual skirt segments 31 is accomplished by suturing with a suture line which is preferably a surgical suture made of polymer material. The fixation in present application is not limited to the suture, and other approaches such as gluing with an adhesive can also be adopted. The present application is not limited to any particular connection between the first protrusion and the skirt segment. For example, the first protrusion and the skirt segment may be fabricated separately and then connected together by suturing. Alternatively, the first protrusion may be integrated with the skirt segment. Likewise, the present application is also not limited to any particular connection between the second protrusion and the skirt segment, which may be either a fixed connection or formed in one piece.

Embodiment 2

Figure 4:
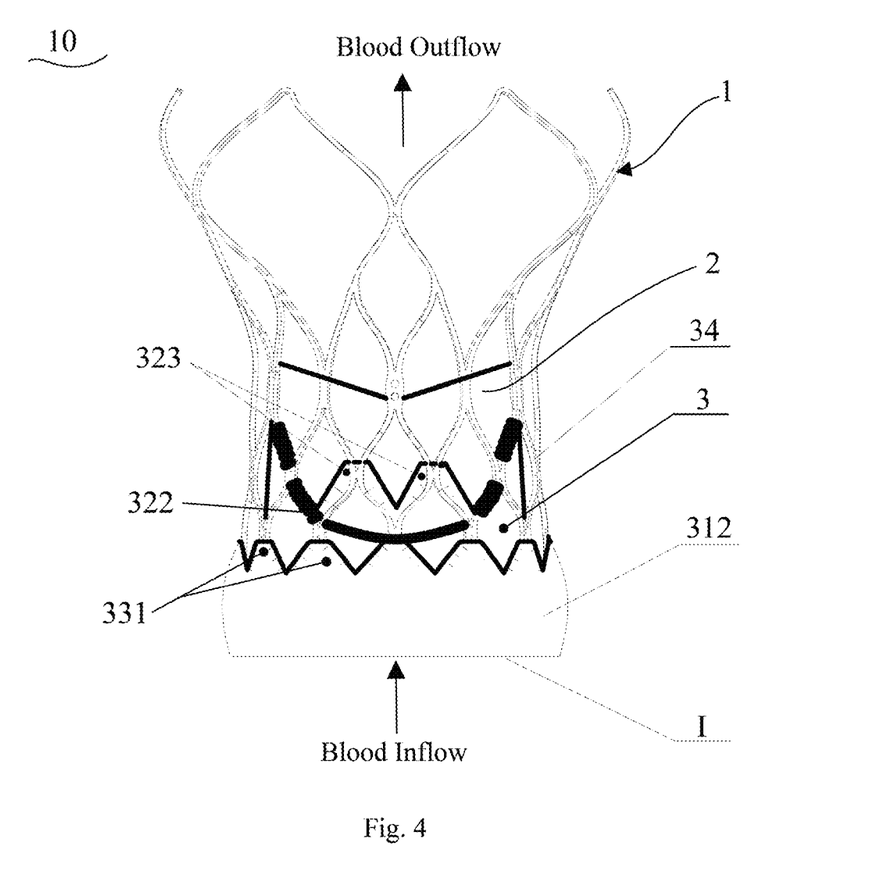
FIG. 4 is a schematic illustration of a valve prosthesis in an expanded state according to embodiment 2 of the present application.
Figure 5:
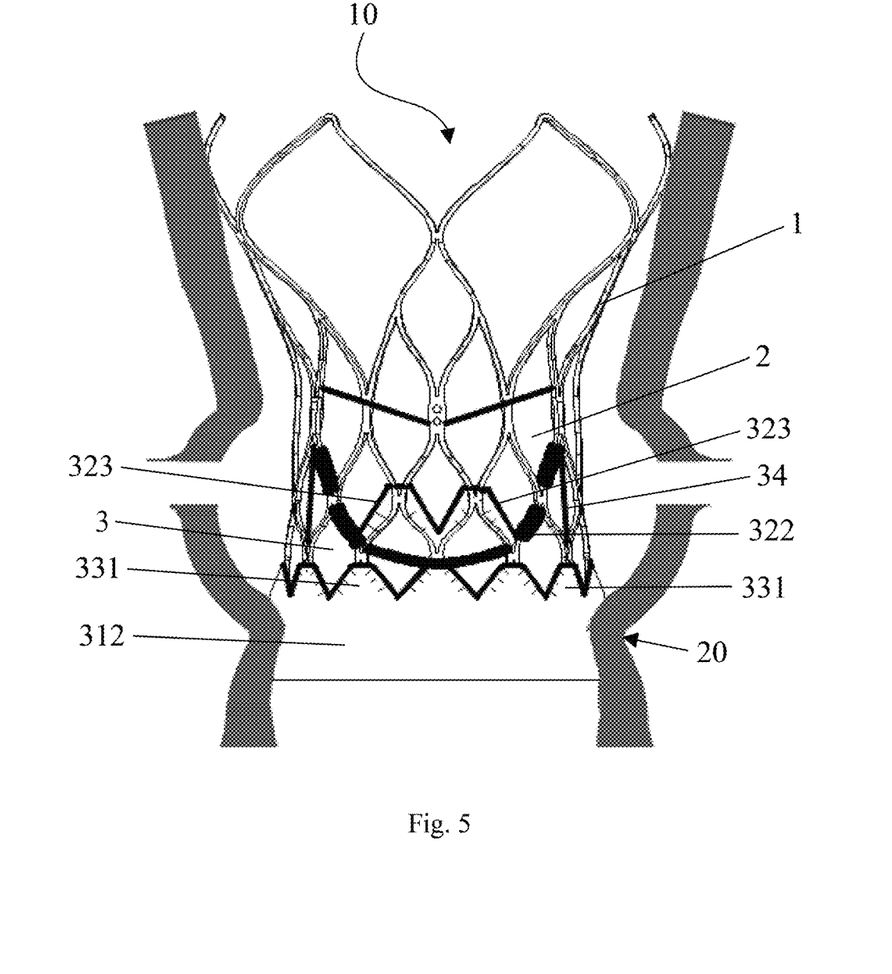
FIG. 5 is a schematic illustration of the valve prosthesis according to embodiment 2 of the present application deployed in the aorta.
Figure 6:
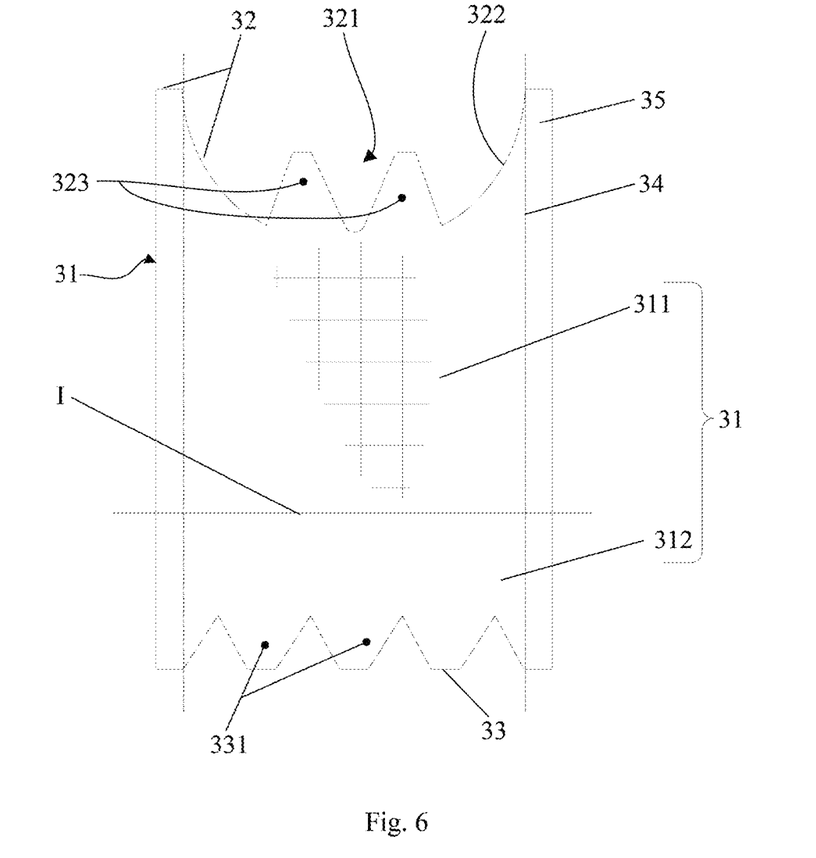
FIG. 6 is a schematic illustration of a skirt segment according to t embodiment 2 of the present application.
Figure 7:
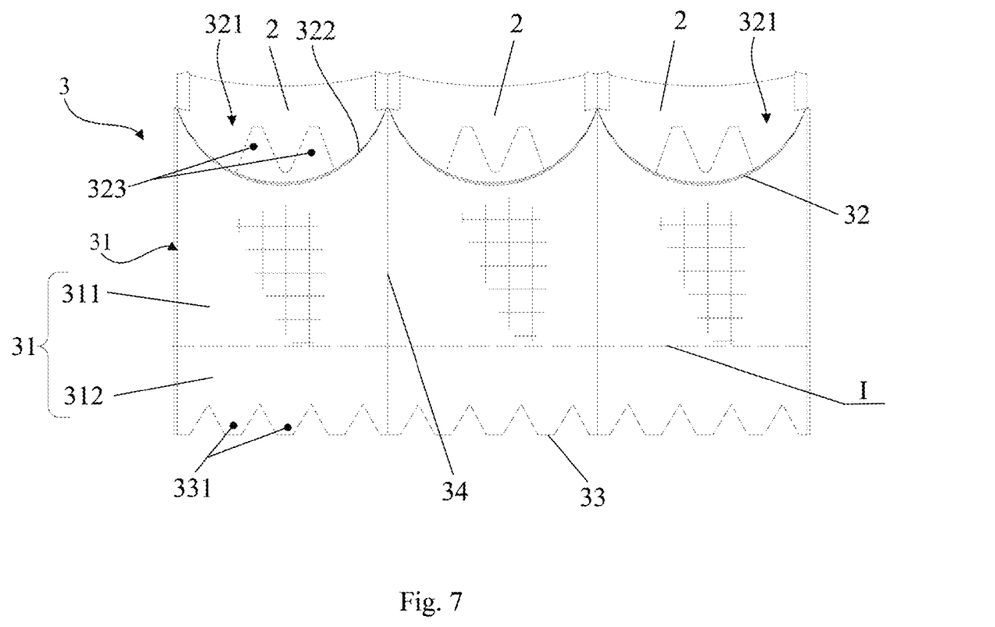
FIG. 7 is a schematic illustration of a skirt assembled with a leaflet according to embodiment 2 of the present application.

Similar to the first embodiment, reference is now made to FIGS. 4 to 7, in which FIG. 4 is a schematic illustration of a valve prosthesis in an expanded configuration according to embodiment 2 of the present application, FIG. 5 is a schematic illustration of the valve prosthesis according to embodiment 1 of the present application deployed in the aorta, FIG. 6 is a schematic illustration of a skirt segment according to embodiment 2 of the present application, and FIG. 7 is a schematic illustration of a skirt assembled with a leaflet according to embodiment 2 of the present application. In this embodiment, an identical element or an element having a same function as Embodiment 1 is given a same reference number.

As shown in FIGS. 4-7, the skirt 3 is constructed from three skirt segments 31 joined together. The upper edge 32 of each skirt segment 31 is provided with a notch 321, and the border of the notch 321 defines a leaflet fixing edge 322 and matches with a corresponding leaflet 2. In other words, each of the skirt segments 31 is fixedly connected to a corresponding leaflet 2 by means of the leaflet fixing edge 322. Further, two first protrusions 323 are arranged in one notch 321, each of the first protrusions extending toward the outflow end of the stent 1 and being fixed to the stent 1.

Differing from Embodiment 1, the skirt 3 according to this embodiment further includes a foldable flap structure arranged outside the stent 1. As shown in FIG. 6, besides the body 311, the skirt segment 31 includes a foldable flap portion 312 extending from the body 311 toward the inflow end of the stent 1, and the foldable flap portion 312 forms the foldable flap structure. In particular, the foldable flap portion 312 has an upper end connected to a lower end of the body 311 (the border line I in FIGS. 6 and 7 indicates a boundary between the bodies 311 and the foldable flap portions 312. It should be noted that border line I is an imaginary line, merely for convenience of explanation) and a lower edge 33 of the skirt segment 31 is located at a lower end of the foldable flap portion 312, the foldable flap portion 312 being fixed to the stent 1 via the lower edge 33. The foldable flap portion 312 may be either integrated with the body 311 or fabricated separately from the body 311 and then assembled therewith. The present application is not limited thereto. Referring to FIG. 5, the foldable flap is able to fill the gap between the stent 1 and the patient tissues after the valve prosthesis 10 is implanted into the patient. In this way, leakage between the stent 1 and the valve annulus 20 due to insufficient deformability of the stent 1 in the expanded configuration is able to be prevented.

Preferably, a length of the body 311 of the skirt segment 31 is 1.5 to 2 times as long as a length of the foldable flap portion 312. If the foldable flap portion 312 is too short, it cannot be sutured to a desired position, resulting in the rupture of the skirt 3 caused by the inflow end portion of the stent 1. If the foldable flap portion 312 is too long, while looseness effect could be ensured, the increased material would increase the whole size of the product. Here, the length of the body 311 of the skirt segment 31 refers to the linear distance from the upper edge 32 of the skirt segment 31 to the lower end of the body 311 (i.e., the location of border line I), and the length of the foldable flap portion 312 refers to the linear distance from the upper end of the foldable flap portion 312 (i.e., the location of border line I) to the lower edge 33 of the skirt segment 31.

During use, as shown in FIG. 4 and FIG. 5, the foldable flap portion 312 is folded from the inflow end of the stent 1 toward the outflow end of the stent 1 and fixed to the outer side of the stent 1. Preferably, the joint line of the foldable flap portion 312 comprises a straight line extending toward the outside of the stent or a curved line protruding toward the outside of the stent. In this way, the foldable flap portion 312 forms a loose structure through suture, enabling to prevent perivalvular leakage more effectively. That is, after the stent 1, the skirt 3 and the leaflets 2 are sutured together, the foldable flap structure of the skirt 3 will not closely adhere to the exterior surface of the stent 1 but leave a gap therebetween.

Further, the skirt includes a second protrusion 331. The second protrusion 331 extends from the lower edge of the foldable flap portion 312 (i.e., the lower edge 33 of the skirt segment 31) and is configured to be fixed to the outer side of the stent 1. That is, one end of the second protrusion 331 is connected to the lower edge 33 of a corresponding skirt segment 31 and the other end of the second protrusion 331 is fixed to the outer side of the stent 1. The second protrusion 331 has a serrated, trapezoidal, sinusoidal shape or other analogous shape, which facilitates its fixation to the stent 1. In one example, the second protrusion 331 is sutured to reticular structure cells of the wavy segment to which the stent is fixed. For example, the second protrusion 331 is sutured to a corresponding reticular structure cell of a first row of the wavy segments from the inflow end of the stent 1 (or sutured to other locations of the stent 1, depending on the actual condition). Fixation to the wavy segments of the first row not only increases preventing height of paravalvular leakage but also increases the connection strength. Compared to embodiments with the second protrusion 331 sutured to, for example, wavy segments of the second row, this arrangement is able to cut down the required material as well as the risk of thrombosis formation.

Similar to the first protrusion 323, the number of the second protrusion(s) 331 depends on the number of reticular structure cells of the wavy segment to which the stent 1 is fixed. In one example, the number of the second protrusions 331 is equal to or less than the number of the reticular structure cells of the said wavy segment. In some examples, the number of the second protrusion(s) 331 ranges from 3 to 12. Preferably, the second protrusions 331 are uniformly arranged at the outer side of the stent 1.

Embodiment 3

In this embodiment, an identical element or an element having a same function is given a same reference number as Embodiment 1. The following description emphasizes the differences between this embodiment and embodiment 1.

In this embodiment, the skirt 3 also comprises an annular structure and is constructed from three skirt segments 31 joined together. The skirt 3 is provided with three notches to match with three leaflets 2, each of the three notches accommodating two first protrusions. Differing from Embodiment 2, each of the three notches includes two notch sections, i.e., a first notch section 321a and a second notch section 321b, each of the two notch sections being located at adjacent upper edges of adjacent skirt segments. In other words, in case that the skirt comprises a plurality of skirt segments, some of the notches each includes two notch sections with the two notch sections being located at two adjacent skirt segments. Alternatively, in case that the skirt includes only one skirt segment, the first notch section 321a and the second notch section 321b are located at the left and right upper edges of the skirt segment. The first protrusion is arranged in the notch section. For example, each notch section is provided with one first protrusion.

Figure 8:
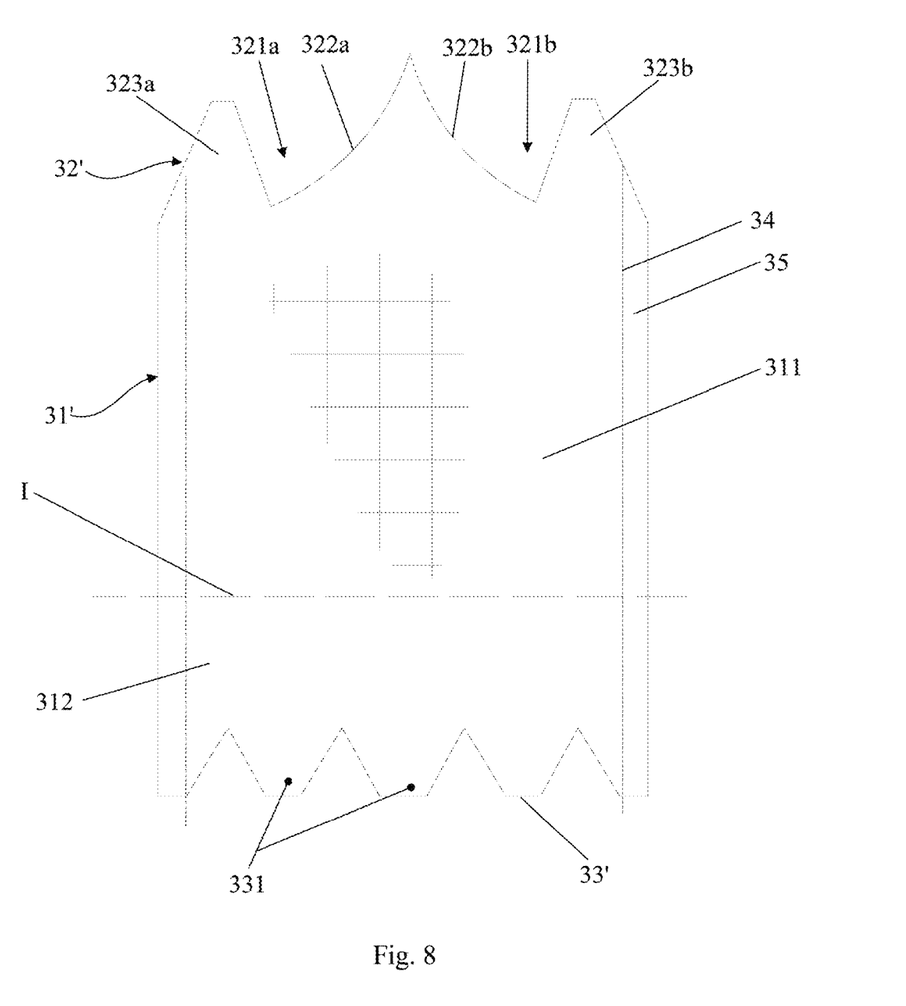
FIG. 8 is a schematic illustration of a skirt segment according to embodiment 3 of the present application.
Figure 9:
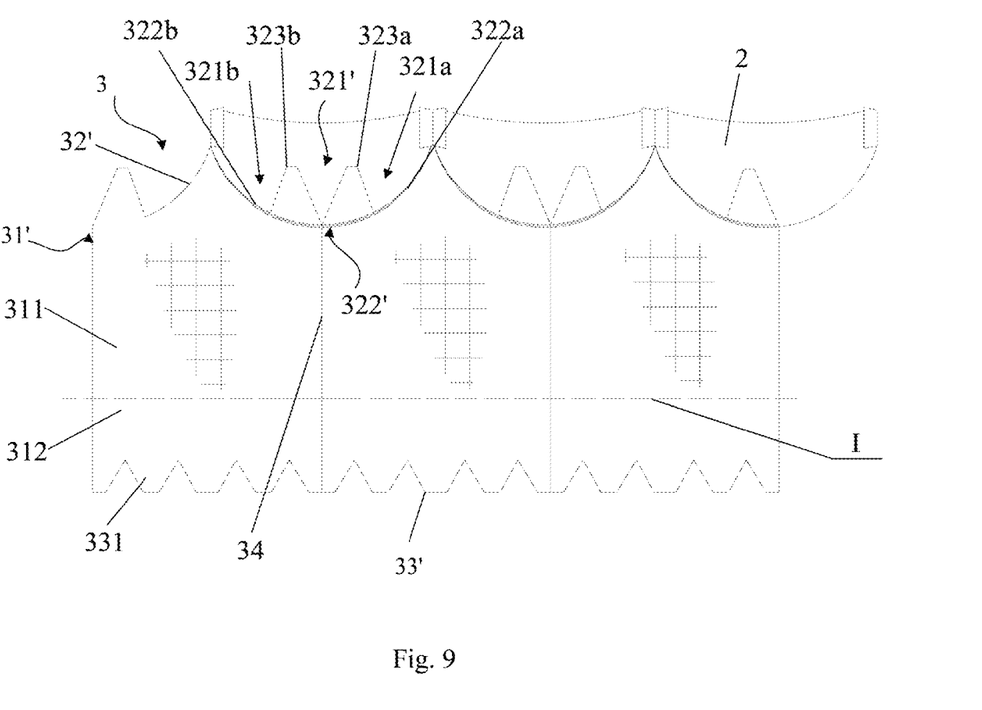
FIG. 9 is a schematic illustration of a skirt according to a preferred example of embodiment 3 of the present application assembled with a leaflet.

As shown in FIG. 8, a skirt segment 31' has an upper edge 32' and a lower edge 33'. The first notch section 321a is arranged at left side of the upper edge 32' of the skirt segment 31' for forming an entire notch with the second notch section 321b of left adjacent skirt segment 31'. The second notch section 321b is arranged at right side of the upper edge 32' of the skirt segment 31' for forming an entire notch with the first notch section 321a of right adjacent skirt segment 31'. Preferably, the first notch section 321a and the second notch section 321b are arranged in symmetry. The first notch section 321a has a first sub-leaflet fixing edge 322a, and the second notch section 321b has a second sub-leaflet fixing edge 322b. As further shown in FIG. 9, the first notch section 321a of the skirt segment 31' forms an entire notch 321' with the second notch section 321b of the left adjacent skirt segment 31', and the first sub-leaflet fixing edge section 322a of the skirt segment 31' forms an entire leaflet fixing edge 322' with the second sub-leaflet fixing edge section 322b of the left adjacent skirt segment 31'. Therefore, the two skirt segments 31' are both fixed to one of the leaflets 2. This applies to the first notch sections 321a of remaining skirt segments 31' and the second notch sections 321b of corresponding adjacent skirt segments 31'. While each of the skirt segments 31' is provided with the first notch section 321a and the second notch section 321b as shown in FIG. 9, it should be appreciated by those skilled in the art that the skirt segment 31' may be provided with only one or none of the first notch section 321a and the second notch section 321b. Furthermore, the number of the notch sections of the skirt 3 should be even so that they can be paired.

In this embodiment, the sub-leaflet fixing edge comprises an inwardly concaved and curved structure protruding toward the lower edge of the skirt segment, preferably an arc structure, more preferably a circular arc structure. In order for the jointed sub-leaflet fixing edges forming a shape of a smooth curve, the sub-leaflet fixing edges preferably have equal radius of curvature at their joint ends. Of course, the leaflet-fixing edge 322' may comprise a structure of other shape, and the present application is not limited in this regard.

With continued reference to FIG. 8, the skirt 3 further comprises two first protrusions 323a and 323b. The first protrusion 323a is arranged on the first notch section 321a, extends toward the outflow end of the stent 1 and is fixed to the stent 1. Similarly, first protrusion 323b is arranged on the second notch section 321b and extends in the same way for fixation to the stent 1. The first protrusions 323a and 323b extending towards the outflow end of the stent 1 are fixed to the stent 1 via, for example, suture operation (see FIGS. 4-5 for the sutured configuration). Preferably, the first protrusions 323a and 323b are arranged in symmetry. According to the present application, fixation of the first protrusion to the stent 1 is able to strengthen connection between the skirt 3 and the stent 1. Besides the ensured connection strength, the first protrusion is also able to increase preventing height of paravalvular leakage, thereby avoiding the leakage of a part of blood from the stent and further improving the paravalvular leakage preventing effect, when the valve prosthesis 10 is implanted slightly lower than desired.

Further, in this embodiment, besides the saw-tooth, trapezoidal and sinusoidal shape, the first protrusion can also have a right-angled triangular or trapezoidal shape. In this way, when two skirt segments 31' are sutured together, the first protrusion 323a of one skirt segment 31' is able to form a saw-tooth or trapezoidal protrusion with the first protrusion 323b of the other skirt segments 31'.

Similar to the above embodiments, adjacent skirt segments 31' are jointed via suture operation, defining a joint line 34 that limits the suture, and two ends of a joint line 34 are located at the junction of two adjacent sub-leaflet fixing edges and the lower edge of the corresponding skirt segment, respectively. Preferably, lengths of adjacent sub-leaflet fixing edges are in a ratio ranging from 1:3 to 3:1. For example, the ratio of the length of the first sub-leaflet fixing edge 322a to the length of the second sub-leaflet fixing edge 322b may be 1:3, 1:2, 1:1, 2:1, 3:1 or other suitable value. In this embodiment, the joint line 34 is a straight line, and one end of the straight line intersects with adjacent sub-leaflet fixing edges 322a and 322b with the other end perpendicularly intersecting the lower edge of the corresponding skirt segment along the straight line. This arrangement allows a shortest joint line 34 between the sub-leaflet fixing edge 322' and the lower edge 33' of the corresponding skirt segment 31', minimizing the number of required stitches in suturing the joint line and further reducing the risk of suture to improve safety in use. However, the present application is not limited to any particular shape of the joint line 34, and the joint line may have an arc or other irregular shape.

In FIG. 9, the sub-leaflet fixing edge 322' is shown as an arc with a symmetric center (i.e., the first sub-leaflet fixing edge 322a and the second sub-leaflet fixing edge section 322b of each skirt segment 31' are identical). Therefore, the intersection point of the joint line 34 and the corresponding leaflet fixing edge 322' coincides with the joint point of the first sub-leaflet fixing edge 322a and the second sub-leaflet fixing edge 322b' and is located at half of the leaflet fixing edge 322'(consisted of the first sub-leaflet fixing edge 322a and the second sub-leaflet fixing edge 322b'), which is the point on the leaflet fixing edge 322' closet to the lower edge 33' of the skirt 3. When suturing the adjacent skirt segments 31' at this point, the formed joint line 34 allows the shortest suture length with the fewest stitches.

In summary, in the valve prosthesis of the present application, the upper portion of the skirt is provided with a first protrusion extending toward the outflow end of the stent and being fixed to the stent. In such a way, on one hand, the connection between the skirt and the stent is able to be strengthened. On the other hand, when the valve prosthesis is implanted slightly lower position than desired, the first protrusion is able to increase preventing height of paravalvular leakage, thereby avoiding the leakage of a part of blood from the stent, and further improving the paravalvular leakage preventing effect.

In particular, the other end of the first protrusion is located at ½ to ⅔ of the height of the leaflets. This enables an increased paravalvular leakage preventing height, ensures a normal operation of valve prosthesis, cuts down skirt's material and reduces the risk of thrombosis formation.

The above description is only a description of the preferred embodiments of the present application, and is not intended to limit the scope of the present application. Any changes and modifications made by those skilled in the art according to the above disclosure are all fall within the protection scope of the appended claims

What is claimed is:

1. A valve prosthesis, comprising a stent, a leaflet and a skirt,
   wherein the stent comprises an inflow end, an outflow end and a plurality of axially connected wavy segments, each of the wavy segments comprising a plurality of reticular structure cells arranged circumferentially, each of the leaflet and the skirt being fixed to the stent, and
   wherein the skirt is comprised of at least one skirt segment, each skirt segment having an upper side close to the outflow end of the stent and a lower side away from the outflow end of the stent, the upper side of the skirt defines a plurality of notches, each of the notches located at the upper side, and the skirt segment is fixed to the leaflet along one notch of the plurality of notches in a side-to-side fashion, wherein the skirt segment further comprises first protrusions extending from the upper side toward the outflow end of the stent, one end of one of the first protrusions being connected to the upper side, another end of the one of the first protrusions being fixed to the stent, wherein the number of the first protrusions in at least one notch of the plurality of notches is two or three, and the upper side of the skirt has a structure of an arc protruding toward a lower side of the skirt.

2. The valve prosthesis of claim 1, wherein the another end of the one of the first protrusions is located at ½ to ⅔ of a height of the leaflet.

3. The valve prosthesis of claim 1, wherein two identical protrusions of the first protrusions are located in the at least one notch.

4. The valve prosthesis of claim 1, wherein the skirt segment further comprises second protrusion(s), one end of the second protrusion being connected to the lower side of the skirt, another end of the second protrusion being fixed to the inflow end of the stent.

5. The valve prosthesis of claim 4, wherein a number of the second protrusion(s) is no more than a number of the reticular structure cells circumferentially arranged at the inflow end of the stent.

6. The valve prosthesis of claim 1, wherein the arc shape protrudes toward the lower side.

7. The valve prosthesis of claim 1, wherein the skirt segment comprises a body and a foldable flap portion extending from the body toward the inflow end of the stent along an axial direction of the stent, wherein the foldable flap portion forms a foldable flap structure by extending along the axial direction of the stent from an inner side of the stent, across the inflow end of the stent, and to an outer side of the stent for filling a gap between the outer side of the stent and a tissue.

8. The valve prosthesis of claim 7, wherein the skirt segment further comprises a second protrusion extending towards the inflow end, one end of the second protrusion being connected to a lower side of the foldable flap portion away from the outflow end, another end of the second protrusion being fixed to the stent at the outer side of the stent.

9. The valve prosthesis of claim 8, wherein the another end of the second protrusion is fixed to a corresponding reticular structure cell of the reticular structure cells of a first row of the wavy segments from the inflow end of the stent.

10. The valve prosthesis of claim 7, wherein along the axial direction of the stent, a length of the body of the skirt segment is 1.5 to 2 times as long as a length of the foldable flap portion.

11. The valve prosthesis of claim 1, wherein lateral sides of the skirt segments are joined together to form joint lines, and wherein joint lines of the foldable flap portion comprises straight lines extending toward an outer side of the stent or curved lines protruding toward the outer side of the stent.

12. The valve prosthesis of claim 1, wherein each of the notches defines two notch sections, and the two notch sections are located at adjacent upper sides of adjacent skirt segments or located at both sides of the upper side of one of the skirt segments.

13. The valve prosthesis of claim 12, wherein each notch section serves as a sub-leaflet fixing side having an arc shape protruding toward the lower side of a corresponding skirt segment.

14. The valve prosthesis of claim 12, wherein a radius of curvature of adjoining sub-leaflet fixing sides are equal at joint ends thereof, and/or
lengths of the adjoining sub-leaflet fixing sides are in a ratio ranging from 1:3 to 3:1.

15. The valve prosthesis of claim 12, wherein the one of the first protrusions is located in a corresponding notch section of the two notch sections and the one of the first protrusions has a serrated, trapezoidal, sinusoidal, right-angled triangular or right-angled trapezoidal shape.

* * * * *